US011572338B2

(12) United States Patent
Nakano et al.

(10) Patent No.: US 11,572,338 B2
(45) Date of Patent: Feb. 7, 2023

(54) METHOD FOR PRODUCING DICYANOCYCLOHEXANE AND BIS(AMINOMETHYL)CYCLOHEXANE

(71) Applicant: MITSUBISHI GAS CHEMICAL COMPANY, INC., Chiyoda-ku (JP)

(72) Inventors: Emi Nakano, Niigata (JP); Noriyuki Shiomi, Niigata (JP); Akifumi Iida, Niigata (JP)

(73) Assignee: MITSUBISHI GAS CHEMICAL COMPANY, INC., Chiyoda-ku (JP)

( * ) Notice: Subject to any disclaimer, the term of this patent is extended or adjusted under 35 U.S.C. 154(b) by 225 days.

(21) Appl. No.: 16/957,210

(22) PCT Filed: Dec. 26, 2018

(86) PCT No.: PCT/JP2018/047809
§ 371 (c)(1),
(2) Date: Jun. 23, 2020

(87) PCT Pub. No.: WO2019/131746
PCT Pub. Date: Jul. 4, 2019

(65) Prior Publication Data
US 2020/0392072 A1  Dec. 17, 2020

(30) Foreign Application Priority Data

Dec. 27, 2017  (JP) .............. JP2017-252013

(51) Int. Cl.
*C07C 253/22* (2006.01)
*C07C 255/46* (2006.01)
(52) U.S. Cl.
CPC .......... *C07C 253/22* (2013.01); *C07C 255/46* (2013.01)
(58) Field of Classification Search
None
See application file for complete search history.

(56) References Cited

U.S. PATENT DOCUMENTS

2013/0197270 A1   8/2013  Yoshimura et al.

FOREIGN PATENT DOCUMENTS

| CN | 105016944 A | 11/2015 |
| JP | 47-23535 B | 6/1972 |
| JP | 63-10752 A | 1/1988 |
| JP | 2008-260757 A | 10/2008 |
| WO | WO 2012/046782 A1 | 4/2012 |

OTHER PUBLICATIONS

Zuffanti, "Ammonium Salts of Aliphatic Carboxylic Acids", Journal of the American Chemical Society, 1941, vol. 63, No. 11, pp. 3123-3124.*
Extended European Search Report dated Feb. 1, 2021 in European Patent Application No. 18897442.2, 5 pages.
András Toró, et al., "Transannular Diels-Alder Studies on the Asymmetric Synthesis of (+)-Maritimol" Tetrahedron, vol. 55, No. 15, XP004223083, Apr. 9, 1999, pp. 4655-4684.
International Search Report dated Apr. 9, 2019 in PCT/JP2018/047809 filed on Dec. 26, 2018, 1 page.
Office Action dated Aug. 30, 2022, in corresponding Japanese Patent Application No. 2019-562095 (with English Translation), 13 pages.

* cited by examiner

*Primary Examiner* — Joseph R Kosack
(74) *Attorney, Agent, or Firm* — Oblon, McClelland, Maier & Neustadt, L.L.P.

(57) ABSTRACT

The problem addressed by this invention is to achieve a useful and novel method for producing dicyanocyclohexane and bis(aminomethyl)cyclohexane. This problem was solved by providing a method for producing dicyanocyclohexane having a cyanation step in which dicyanocyclohexane is obtained by a cyanation reaction of cyanocyclohexane-1-carboxylic acid and/or a salt thereof with an ammonia source, and a method for producing bis(aminomethyl)cyclohexane using the dicyanocyclohexane thus produced.

20 Claims, No Drawings

METHOD FOR PRODUCING DICYANOCYCLOHEXANE AND BIS(AMINOMETHYL)CYCLOHEXANE

TECHNICAL FIELD

The present invention relates to a method for producing dicyanocyclohexane such as 1,4-dicyanocyclohexane and bis(aminomethyl)cyclohexane such as 1,4-bis(aminomethyl)cyclohexane.

BACKGROUND ART

Bis(aminomethyl)cyclohexane is an industrially important compound that is used as a raw material of an epoxy curing agent, a polyamide, a polyurethane and the like. Since such bis(aminomethyl)cyclohexane is obtained through hydrogenation reaction of dicyanocyclohexane, methods for efficiently producing this dicyanocyclohexane have been explored. For example, a method in which cyclohexane dicarboxylic acid diester is cyanated in the presence of an ammonia source cyanation (for example, Patent document 1), a method in which cyclohexanediamide is heated (for example, Patent document 2) and a method in which cyclohexane dicarboxylic acid is heated and cyanated in the presence of an ammonia source without a solvent (for example, Patent document 3) are known.

CITATION LIST

Patent Literature

Patent document 1: Japanese Laid-Open Patent Publication No. Showa 63(1988)-010752
Patent document 2: Chinese Patent Publication No. 105016944
Patent document 3: International Patent Publication WO2012/046782

SUMMARY OF INVENTION

Technical Problem

Some conventional production methods have a problem of being incapable of producing dicyanocyclohexane in an efficiently way. For example, if a step of cyanating a diester such as cyclohexane dicarboxylic acid dimethyl through reaction with an ammonia source is employed, alcohol such as methanol is produced as a by-product along with the generation of dicyanocyclohexane, namely, the compound of interest. Since this alcohol reacts with the ammonia source to produce an alkylamine such as methylamine, and an amide as a by-product is further produced from the alkylamine and the ester as the raw material, the yield of the compound of interest is deteriorated and a by-product that is hard to separate is generated.

Furthermore, if dicyanocyclohexane is produced by using cyclohexane dicarboxamide that has a high melting point (for example, melting point of trans-1,4-cyclohexane dicarboxamide is 345 to 350° C.) or the like as a raw material, it would be hard to melt and dissolve the raw material and thus efficiency enhancement and energy saving of the production method are impeded. Similar to cyclohexane dicarboxamide, the same problem may occur when cyclohexane dicarboxylic acid with a high melting point (for example, melting point of trans-1,4-cyclohexane dicarboxylic acid is 285 to 321° C.) is used as a raw material without a solvent.

The present invention was made mainly in view of the above-described problems, and has an objective of providing a novel and useful method for producing dicyanocyclohexane, i.e., a precursor of bis(aminomethyl)cyclohexane, and bis(aminomethyl)cyclohexane.

Solution to Problem

The present inventors have gone through intensive investigation to achieve the above-described objective, and as a result of which they found that dicyanocyclohexane and bis(aminomethyl)cyclohexane can be produced in an efficient way by reducing the number of steps without generating a by-product that is hard to separate, by using a specific compound as a raw material without a solvent or, if necessary, with a solvent, thereby accomplishing the present invention.

Thus, the present invention is as follows.

(1) A method for producing dicyanocyclohexane, the method comprising a cyanation step in which cyanocyclohexane-1-carboxylic acid and/or a salt thereof is subjected to cyanation reaction with an ammonia source to obtain dicyanocyclohexane.

(2) The method for producing dicyanocyclohexane according to (1) above, wherein the cyanocyclohexane-1-carboxylic acid comprises 2-cyanocyclohexane-1-carboxylic acid, 3-cyanocyclohexane-1-carboxylic acid or 4-cyanocyclohexane-1-carboxylic acid.

(3) The method for producing dicyanocyclohexane according to either one of (1) and (2) above, further comprising a raw material producing step in which cyclohexane dicarboxylic acid and/or a salt thereof and dicyanocyclohexane are heated to obtain a mixture of the cyanocyclohexane-1-carboxylic acid and/or a salt thereof, the cyclohexane dicarboxylic acid and/or a salt thereof and the dicyanocyclohexane.

(4) The method for producing dicyanocyclohexane according to (3) above, wherein the raw material producing step comprises heating a mixture of the dicyanocyclohexane and the cyclohexane dicarboxylic acid and/or a salt thereof at a weight ratio of 0.3 to 7.8.

(5) The method for producing dicyanocyclohexane according to either one of (3) and (4) above, wherein, in the raw material producing step, the amount of the cyanocyclohexane-1-carboxylic acid produced by heating is 20 to 100 mol % relative to the cyclohexane dicarboxylic acid before heating.

(6) The method for producing dicyanocyclohexane according to any one of (3) to (5) above, wherein a catalyst comprising at least zinc oxide, tin oxide or iron oxide is used in the cyanation step.

(7) The method for producing dicyanocyclohexane according to any one of (1) to (6) above, wherein the ammonia source comprises ammonia, urea, ammonium hydrogen carbonate or ammonium carbonate.

(8) The method for producing dicyanocyclohexane according to any one of (1) to (7) above, wherein the mole ratio between the ammonia source and the cyanocyclohexane-1-carboxylic acid and/or a salt thereof used in the cyanation step is 0.1 to 5.

(9) The method for producing dicyanocyclohexane according to any one of (1) to (8) above, wherein the boiling point of at least one solvent used in the cyanation step is 600° C. or lower.

(10) The method for producing dicyanocyclohexane according to any one of (1) to (9) above, wherein the weight ratio of the solvent to the cyanocyclohexane-1-carboxylic acid and/or a salt thereof used in the cyanation step is 10 or less.

(11) The method for producing dicyanocyclohexane according to any one of (1) to (10) above, wherein the reaction temperature in the cyanation step is 150° C. to 350° C.

(12) The method for producing dicyanocyclohexane according to any one of (1) to (11) above, wherein the reaction pressure in the cyanation step is 0.001 MPa to 10 MPa.

(13) The method for producing dicyanocyclohexane according to any one of (1) to (12) above, wherein the salt of the cyanocyclohexane-1-carboxylic acid comprises an ammonium salt.

(14) The method for producing dicyanocyclohexane according to any one of (3) to (13) above, wherein the salt of the cyclohexane dicarboxylic acid comprises an ammonium salt.

(15) A method for producing bis(aminomethyl)cyclohexane, the method comprising an amination step in which the dicyanocyclohexane obtained by the method for producing dicyanocyclohexane according to any one of (1) to (14) above is subjected to hydrogenation reaction to obtain bis(aminomethyl)cyclohexane.

Advantageous Effects of the Invention

The present invention can realize a method for producing dicyanocyclohexane and a method for producing bis(aminomethyl)cyclohexane, which are capable of enhancing the efficiency of the reaction and/or enhancing the yield without generating a by-product that is hard to separate from the reaction system by using a raw material substance having a relatively low melting point.

DESCRIPTION OF EMBODIMENT

Hereinafter, modes for carrying out the present invention will be described in detail, although the present invention should not be limited to the following embodiments. The present invention can be modified in various ways without departing from the scope of the invention.

1. Cyanation Step

A method for producing dicyanocyclohexane according to this embodiment comprises a cyanation step in which cyanocyclohexane-1-carboxylic acid is subjected to cyanation reaction with an ammonia source to obtain dicyanocyclohexane. The outline of the cyanation step is represented by in Formula (I) below.

[Chemical formula 1]

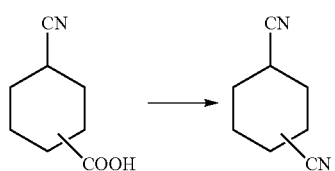

(I)

Cyanocyclohexane-1-carboxylic acid used in the cyanation step is preferably one that has a cyano group at position 2, 3 or 4, specifically, 2-cyanocyclohexane-1-carboxylic acid represented by Formula (a) below, 3-cyanocyclohexane-1-carboxylic acid represented by Formula (b) below or 4-cyanocyclohexane-1-carboxylic acid represented by Formula (c) below. In the cyanation step, one or two or more of 2-cyanocyclohexane-1-carboxylic acid, 3-cyanocyclohexane-1-carboxylic acid, 4-cyanocyclohexane-1-carboxylic acid and salts thereof can be used alone or in combination. Furthermore, cyanocyclohexane-1-carboxylic acid of the present embodiment represented by any of Formulae (a)-(c) below may be any of a cis isomer, a trans isomer or a mixture of a cis isomer and a trans isomer.

[Chemical formula 2]

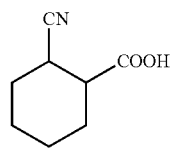
(a)

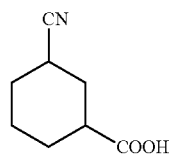
(b)

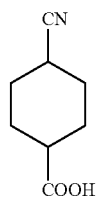
(c)

Specifically, preferable examples of the salt of cyanocyclohexane-1-carboxylic acid used in the cyanation step include alkali metal salts such as a sodium salt and a potassium salt, and a more preferable example includes an ammonium salt.

In the cyanation step, a salt of any of 2-cyanocyclohexane-1-carboxylic acid, 3-cyanocyclohexane-1-carboxylic acid and 4-cyanocyclohexane-1-carboxylic acid, or a mixture of such salts may be used. Alternatively, a mixture of at least one of 2-cyanocyclohexane-1-carboxylic acid, 3-cyanocyclohexane-1-carboxylic acid and 4-cyanocyclohexane-1-carboxylic acid, and at least one of the aforementioned salts of cyanocyclohexane-1-carboxylic acid may be used in the cyanation step.

Accordingly, since cyanocyclohexane-1-carboxylic acid according to the present embodiment also comprises a salt form, "cyanocyclohexane-1-carboxylic acid and/or a salt thereof" is hereinafter also simply referred to as "cyanocyclohexane-1-carboxylic acid".

As the ammonia source, ammonia, urea, ammonium hydrogen carbonate, ammonium carbonate and the like can favorably be used. One or more of them may be used as a mixture. When ammonia is used as the ammonia source, it is preferably used as ammonia gas.

The mole ratio of the ammonia source and cyanocyclohexane-1-carboxylic acid and/or a salt thereof (number of moles of the ammonia source/number of moles of cyanocyclohexane-1-carboxylic acid) used in the cyanation step is preferably 0.1 to 5, more preferably 0.3 to 4 and particularly preferably in a range of 0.5 to 3. Here, when gas such as ammonia gas is used as the ammonia source, the number of moles of the total flow rate per hour is considered to be the number of moles of the ammonia source.

The cyanation step may be carried out with or without a solvent, where preferably a solvent having a boiling point of 600° C. or lower, more preferably a solvent having a boiling point of 500° C. or lower and still more preferably a solvent having a boiling point of 420° C. or lower is used. Moreover, the boiling point of the solvent, which is higher than the reaction temperature of the cyanation reaction, is preferably 250° C. or higher, more preferably 270° C. or higher and still more preferably 300° C. or higher. A boiling point of 300° C. or higher allows the cyanation reaction to proceed smoothly and is also likely to suppress generation of impurities such as a trimer of dicyanocyclohexane.

Examples of the solvent used in the cyanation step include aliphatic alkanes such as heptadecane, nonadecane and docosane; aliphatic alkenes such as heptadecene, nonadecene and docosene; aliphatic alkynes such as heptadecyne, nonadecyne and docosyne; alkyl-substituted aromatics, for example, alkylbenzene such as undecylbenzene, tridecylbenzene and tetradecylbenzene, dialkylbenzene and alkylnaphthalene; acids and acid anhydrides such as 2,5-dichlorobenzoic acid and tetrachlorophthalic anhydride; amide compounds such as undecanamide, lauramide and stearamide; nitrile compounds such as tetradecanenitrile, hexadecanenitrile, 2-naphthylacetonitrile, stearonitrile and 1,4-dicyanocyclohexane; phosphorus compounds such as p-chlorodiphenylphosphine and triphenyl phosphite; amines such as 1,2-diphenylethylamine and trioctylamine; hydroxides such as 2,2'-biphenol and triphenylmethanol; esters such as benzyl benzoate and dioctyl phthalate; ethers such as 4-dibromophenyl ether; halogenated benzenes such as 1,2, 4,5-tetrachloro-3-nitrobenzene and 4,4'-dichlorobenzophenone; ketones such as 2-phenylacetophenone and anthraquinone, and triphenylmethane; and the like.

Among them, alkylnaphthalene, triphenylmethane, dicyanocyclohexane and the like are favorable in that they do not hinder the cyanation reaction.

While the solvent in the cyanation step may be used in any amount as long as the cyanation reaction sufficiently proceeds, a solvent is either not used or used in an amount such that the weight ratio of the solvent and the raw material cyanocyclohexane-1-carboxylic acid and/or a salt thereof (weight (g) of solvent (except the later-described dicyanocyclohexane)/weight (g) of cyanocyclohexane-1-carboxylic acid) is preferably 10 or less, more preferably 0.01 to 10, still more preferably 0.05 to 5 and particularly preferably in a range of 0.1 to 3.

In order to dissolve cyanocyclohexane-1-carboxylic acid or a salt thereof, i.e., the raw material, in the cyanation step, dicyanocyclohexane which is also the target substance may be used as the solvent. Moreover, the weight ratio of dicyanocyclohexane used as the solvent (weight (g) of solvent/weight (g) of cyanocyclohexane-1-carboxylic acid) is determined without including dicyanocyclohexane used in the raw material producing step in the amount of the solvent.

The reaction temperature in the cyanation step is preferably 150° C. to 350° C., more preferably 200° C. to 340° C., still more preferably 230° C. to 330° C. and particularly preferably in a range of 250° C. to 320° C.

Moreover, while the reaction pressure in the cyanation step may be negative, atmospheric or positive, it is preferably 0.001 MPa to 10 MPa, more preferably 0.05 MPa to 5 MPa and still more preferably in a range of 0.08 MPa to 0.12 MPa, and it is, for example, atmospheric (0.1 MPa).

A catalyst is preferably used for the cyanation reaction for obtaining dicyanocyclohexane from cyanocyclohexane-1-carboxylic acid or a salt thereof. The catalyst used may be either homogeneous or heterogeneous.

As the catalyst, a catalyst that is generally used for cyanation reaction can be used, where specific examples include metal oxides such as silica gel, alumina, silica-alumina, hydrotalcite, magnesium oxide, zinc oxide, tin oxide, iron oxide, titanium oxide, zirconium oxide, hafnium oxide, manganese oxide, tungsten oxide, vanadium pentoxide, niobium pentoxide, tantalum oxide, gallium oxide, indium oxide and scandium oxide, which may be used alone, may be used as a complex oxide or may be used as a supported oxide.

Examples of a support component include alkali metals such as sodium, lithium, potassium, rubidium and cesium, tin, rhenium, manganese, molybdenum, tungsten, vanadium, iron, nickel, zinc, chromium, boric acid, hydrochloric acid and phosphoric acid.

A catalyst in which an active element, i.e., the above-mentioned metal catalyst, is supported by one or two or more generally used supports such as carbon, hydrotalcite, MgO, $Al_2O_3$, $SiO_2$, $SiO_2$—$Al_2O_3$, $TiO_2$ or $ZrO_2$ may be used. If a support is to be used, the amount of the metal catalyst as the active element is preferably 0.1 to 10 mass % relative to 100 mass % of the support.

Examples of the catalyst further include rhenium compounds such as perrhenic acid and rhenium oxide, organic tin compounds such as dibutyltin oxide, ruthenium compounds such as dichlorotris(triphenylphosphine)ruthenium (II), and cobalt oxide.

Among them, a catalyst that contains zinc oxide, tin oxide or iron oxide is favorable in that they are more effective and reliable to carry out the cyanation reaction. One or two or more catalysts may be used alone or in combination. Furthermore, the amount of the catalyst used is preferably 0.05 to 20 mass % relative to 100 mass % of cyanocyclohexane-1-carboxylic acid, cyclohexane dicarboxylic acid or a salt thereof. By making the amount of the catalyst to lie in the above-mentioned range, the yield of the resulting dicyanocyclohexane can be increased. The above-described catalyst may be present not only during the cyanation step but also during the raw material producing step.

2. Raw Material Producing Step

While isolated cyanocyclohexane-1-carboxylic acid can be used as a raw material in the method for producing dicyanocyclohexane according to the present embodiment, cyanocyclohexane-1-carboxylic acid that is not isolated or a precursor thereof can also be used. Specifically, cyclohexane dicarboxylic acid may be used with a nitrile compound or the like for cyanating with said cyclohexane dicarboxylic acid to generate cyanocyclohexane-1-carboxylic acid, or dicyanocyclohexane may be used with a compound having a carboxy group for carboxylating with said dicyanocyclohexane to generate cyanocyclohexane-1-carboxylic acid. Preferably, the method may comprise a raw material producing step in which cyclohexane dicarboxylic acid and dicyanocyclohexane are heated to obtain cyanocyclohexane-1-carboxylic acid through the reaction represented by Formula (II) below, namely, cyanation of cyclohexane dicarboxylic acid.

[Chemical formula 3]

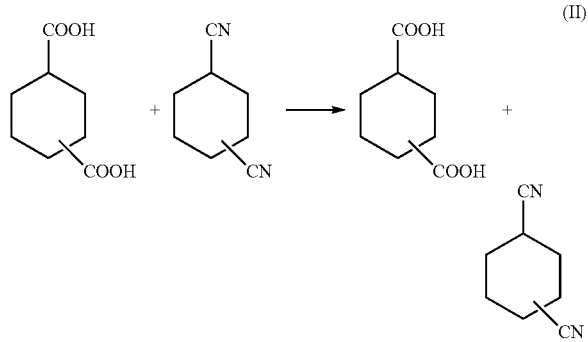

Accordingly, by intentionally using dicyanocyclohexane, i.e., the compound of interest, as a solvent together with cyclohexane dicarboxylic acid, i.e., the raw material, in the raw material producing step, cyanocyclohexane-1-carboxylic acid having a melting point lower than that of cyclohexane dicarboxylic acid can be generated without requiring an isolation step. As a result, the efficiency of the reaction that results dicyanocyclohexane can be enhanced.

Cyclohexane dicarboxylic acid used in the raw material producing step is preferably 1,2-cyclohexane dicarboxylic acid, 1,3-cyclohexane dicarboxylic acid or 1,4-cyclohexane dicarboxylic acid. In the raw material producing step, one or two or more of 1,2-cyclohexane dicarboxylic acid, 1,3-cyclohexane dicarboxylic acid, 1,4-cyclohexane dicarboxylic acid and a salt thereof may be used alone or in combination. Furthermore, any of a cis isomer, a trans isomer or a mixture of a cis isomer and a trans isomer may be used as cyclohexane dicarboxylic acid of the present embodiment.

While a salt of cyanocyclohexane-1-carboxylic acid may be used in the cyanation step as described above, a salt of cyclohexane dicarboxylic acid may also be used in the raw material producing step, where the salt may be either a mono-salt or a di-salt. Specifically, preferable examples of the salt of cyclohexane dicarboxylic acid include alkali metal salts such as a sodium salt, a potassium salt and an ammonium salt, and a more preferable example includes an ammonium salt.

In the raw material producing step, any of the above-mentioned salts of cyclohexane dicarboxylic acid or a mixture of these salts may be used. Alternatively, a mixture containing at least any of 1,2-cyclohexane dicarboxylic acid, 1,3-cyclohexane dicarboxylic acid and 1,4-cyclohexane dicarboxylic acid, and at least any of the above-mentioned salts of cyclohexane dicarboxylic acid may be used in the raw material producing step.

In the raw material producing step, cyclohexane dicarboxylic acid and/or a salt thereof and dicyanocyclohexane can be heated to obtain a mixture of cyanocyclohexane-1-carboxylic acid and/or a salt thereof, cyclohexane dicarboxylic acid and/or a salt thereof, and dicyanocyclohexane.

Accordingly, since cyclohexane dicarboxylic acid of the present embodiment also comprises a form of a salt, "cyclohexane dicarboxylic acid and/or a salt thereof" hereinafter may also be simply referred to as "cyclohexane dicarboxylic acid".

Thus, in the raw material producing step, cyclohexane dicarboxylic acid and dicyanocyclohexane are preferably mixed in advance and cyclohexane dicarboxylic acid is cyanated while heating this mixture.

The weight ratio of dicyanocyclohexane and cyclohexane dicarboxylic acid (weight (g) of dicyanocyclohexane/weight (g) of cyclohexane dicarboxylic acid and/or a salt thereof) in such a mixture in the raw material producing step is preferably 0.3 to 7.8, more preferably 0.5 to 3.9 and particularly preferably 0.7 to 2.4.

In the raw material producing step, however, other solvent apart from dicyanocyclohexane may also be used.

The reaction temperature in the raw material producing step is preferably 150° C. to 350° C., more preferably 200° C. to 340° C., still more preferably 230° C. to 330° C. and particularly preferably in a range of 250° C. to 320° C.

Moreover, while the reaction pressure in the raw material producing step may be negative, atmospheric or positive, it is preferably 0.001 MPa to 10 MPa, more preferably 0.05 MPa to 5 MPa and still more preferably in a range of 0.08 MPa to 0.12 MPa, and it is, for example, atmospheric (0.1 MPa).

Alternatively, if the raw material producing step is to be employed, dicyanocyclohexane can be produced via a series of continuous reaction processes without isolating cyanocyclohexane-1-carboxylic acid, as represented in Formula (III) below. Accordingly, since dicyanocyclohexane can be generated without isolating cyanocyclohexane-1-carboxylic acid, the method for producing dicyanocyclohexane of the present embodiment can further enhance the production efficiency.

[Chemical formula 4]

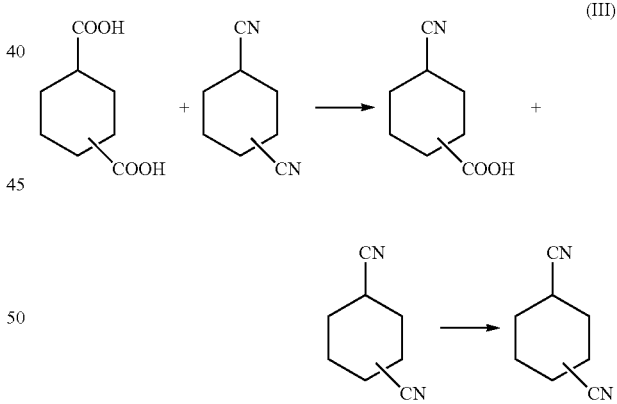

3. Amination Step

The method for producing bis(aminomethyl)cyclohexane of the present embodiment comprises an amination step represented by Formula (IV) below in which dicyanocyclohexane obtained by the above-described production method is subjected to hydrogenation reaction (hereinafter, also referred to as "nitrile hydrogenation reaction") to obtain bis(aminomethyl)cyclohexane. 1,2-dicyanocyclohexane, 1,3-dicyanocyclohexane and 1,4-dicyanocyclohexane result 1,2-bis(aminomethyl)cyclohexane, 1,3-bis(aminomethyl)cyclohexane and 1,4-bis(aminomethyl)cyclohexane, respectively.

[Chemical formula 5]

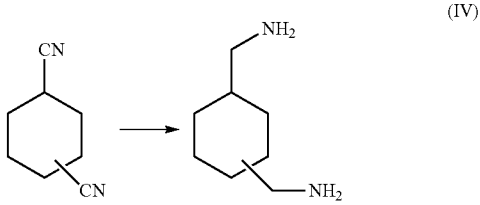

(IV)

In the amination step, first, dicyanocyclohexane, a solvent and a catalyst are placed in a reactor, into which hydrogen gas is introduced until a predetermined pressure is obtained in the system. Subsequently, the resultant is heated until a predetermined temperature is obtained inside the reactor to allow nitrile hydrogenation reaction to proceed while appropriately introducing hydrogen gas into the reactor such that the pressure inside the reactor is kept within a certain range.

As the solvent, a solvent that is generally used for nitrile hydrogenation reaction can be used, where specific examples include alcohols such as methanol, ethanol, 1-propanol, 2-propanol, 1-butanol, 2-butanol and tert-butanol, aromatic hydrocarbons such as meta-xylene, mesitylene and pseudocumene, liquid ammonia, and aqueous ammonia. One or two or more solvents may be used alone or in combination.

As the catalyst used in the amination step, a catalyst that is generally used for nitrile hydrogenation reaction can be employed. Specifically, a catalyst containing Ni and/or Co may be used. In general, a catalyst in which Ni and/or Co is supported by $Al_2O_3$, $SiO_2$, diatomite, $SiO_2$—$Al_2O_3$ or $ZrO_2$ by precipitation, Raney nickel or Raney cobalt can favorably be used as the catalyst. Among them, Raney cobalt catalyst and Raney nickel catalyst are favorable in that they are more effective and reliable to carry out the nitrile hydrogenation reaction. One or two or more catalysts can be used alone or in combination.

The amount of the above-described catalyst used is preferably 0.1 to 150 mass %, more preferably 0.1 to 20 mass % and still more preferably 0.5 to 15 mass % relative to 100 mass % of dicyanocyclohexane. By using the catalyst in an amount within this range, the yield of the resulting bis(aminomethyl)cyclohexane can be increased.

The concentration of dicyanocyclohexane in the amination step is preferably 1 to 50 mass % and more preferably 2 to 40 mass % relative to the whole amount of the reaction solution from the viewpoint of reaction efficiency.

The reaction temperature in the amination step is preferably 40 to 150° C., preferably 60 to 130° C. and more preferably in a range of 80 to 120° C.

The reaction pressure in the amination step is preferably 0.5 MPa to 15 MPa, more preferably 0.7 MPa to 10 MPa and still more preferably in a range of 1 MPa to 8 MPa in terms of the partial pressure of hydrogen.

The length of time of the nitrile hydrogenation reaction in the amination step may be any length as long as the hydrogenation sufficiently proceeds.

By adjusting the reaction conditions to lie within the aforementioned ranges, the yield and the selectivity of the resulting bis(aminomethyl)cyclohexane can be increased.

EXAMPLES

Hereinafter, the present invention will be described in more detail by way of examples. The present invention, however, should not be limited to the following examples, and can be modified and carried out without departing from the scope of the present invention.

Example 1

In Example 1, cyanocyclohexane-1-carboxylic acid was cyanated to obtain dicyanocyclohexane.

(Production of Dicyanocyclohexane by Using Cyanocyclohexane-1-Carboxylic Acid)

88.9 g of 4-cyanocyclohexane-1-carboxylic acid (which did not contain salts except as the faintest trace of impurities), 0.2 g of zinc oxide (from Kanto Chemical Co., Inc) and 50.0 g of 1,4-dicyanocyclohexane were fed into a 300-mL five-necked separable flask equipped with a stirring blade, a gas feeding pipe capable of changing the feeding height, a thermocouple and a dehydrator. The temperature was raised, and nitrogen gas (feeding rate 34 ml/min) and ammonia gas (feeding rate 174 ml/min) were introduced into the flask via the gas feeding pipe placed above the liquid surface while stirring at 300 rpm at 170° C. Once the temperature of the reaction system reached 270° C., the gas inlet was brought down into the reaction solution to initiate bubbling, which was considered as the start time of the cyanation reaction. The temperature of the reaction system was further raised to stir for 7 hours at a reaction temperature of 300° C.

At the end of the reaction, the reaction system was left to cool to room temperature, the reaction product was dissolved in methanol and analyzed by gas chromatography (hereinafter, also referred to as GC). As a result, the conversion rate of 4-cyanocyclohexane-1-carboxylic acid and the yield of 1,4-dicyanocyclohexane were 99.9% and 91.0%, respectively.

<GC Analysis Conditions>

Analyzer: Type name "GC2010 PLUS" from Shimadzu Corporation

Column: Product name "HP-5 ms" (from Agilent Technologies, Inc., length 30 m×inner diameter 0.25 mm, thickness 0.25 μm)

Carrier gas: He (constant pressure: 73.9 kPa)

Temperature at inlet: 300° C.

Detector: FID

Temperature of detector: 300° C.

Temperature of column oven: starting at 100° C., raised to 300° C. at 10° C./min and kept at 300° C. for 30 minutes Example 2

In Example 2, cyclohexane dicarboxylic acid was converted to cyanocyclohexane-1-carboxylic acid in the reaction system, and then cyanocyclohexane-1-carboxylic acid was further cyanated without being isolated to give dicyanocyclohexane.

(One-Pot Production of Dicyanocyclohexane)

100 g of 1,4-cyclohexane dicarboxylic acid (which did not contain salts except as the faintest trace of impurities: Tokyo Chemical Industry Co., Ltd.), 1.6 g of zinc oxide and 100 g of 1,4-dicyanocyclohexane were fed into a 500-mL five-necked flask equipped with a stirring blade, a gas feeding pipe capable of changing the feeding height, a thermocouple and a dehydrator. Nitrogen gas (feeding rate 68 ml/min) and ammonia gas (feeding rate 348 ml/min) were introduced into the flask via the gas feeding pipe placed above the liquid surface while stirring at 300 rpm at 170° C. Once the temperature of the reaction system reached 270° C., the gas inlet was brought down into the reaction solution to initiate bubbling, which was considered as the start time of the cyanation reaction. The temperature of the reaction system was further raised to stir for 7 hours at a reaction temperature of 300° C.

At the end of the reaction, the reaction system was left to cool to room temperature, the reaction product was dissolved in methanol and analyzed by GC. As a result, the conversion rate of 1,4-cyclohexane dicarboxylic acid and the yield of 1,4-dicyanocyclohexane were 99.9% and 90.8%, respectively.

(Production of bis(aminomethyl)cyclohexane)

24.4 g of 1,4-dicyanocyclohexane, 37.3 g of methanol and 28.4 g of 28% aqueous ammonia (from Wako Pure Chemical Industries, Ltd.) as solvents, and 0.56 g of Raney cobalt catalyst (from Wako Pure Chemical Industries, Ltd.) as a catalyst were fed into a 300-mL SUS316-made pressure-resistant vessel, into which hydrogen gas was introduced until a reaction pressure of 4.5 MPa was obtained. Subsequently, the reaction temperature inside the vessel was raised to 80° C. and kept at a constant temperature to allow amination reaction by hydrogenation (nitrile hydrogenation reaction) to proceed for 240 minutes while stirring inside the vessel with an electromagnetic stirring blade at 750 rpm. As a result, the conversion rate of 1,4-dicyanocyclohexane and the selectivity and the yield of 1,4-bis(aminomethyl)cyclohexane were 100%, 97.0% and 97.0%, respectively.

Example 3

In Example 3, cyanation reaction was carried out in the same manner as Example 2 except that ammonium salt of 1,4-cyclohexane dicarboxylic acid was used as the raw material.

(One-Pot Production of Dicyanocyclohexane by Using Ammonium Salt of Cyclohexane Dicarboxylic Acid)

51.6 g of ammonium salt of 1,4-cyclohexane dicarboxylic acid (where the ammonia content in 1,4-cyclohexane dicarboxylic acid ammonium salt to the 1,4-cyclohexane dicarboxylic acid content in 1,4-cyclohexane dicarboxylic acid ammonium salt was 0.34 in a mole ratio), 0.20 g of zinc oxide as a catalyst and 50 g of 1,4-dicyanocyclohexane were fed into a 300-mL five-necked separable flask equipped with a stirring blade, a gas feeding pipe capable of changing the feeding height, a thermocouple and a dehydrator. Nitrogen gas (feeding rate 34 ml/min) and ammonia gas (feeding rate 174 ml/min) were introduced into the flask via the gas feeding pipe placed above the liquid surface while stirring at 300 rpm at 170° C. Once the temperature of the reaction system reached 270° C., the gas inlet was brought down into the reaction solution to initiate bubbling, which was considered as the start time of the cyanation reaction. The temperature of the reaction system was further raised to stir for 7 hours at a reaction temperature of 300° C.

At the end of the reaction, the reaction system was left to cool to room temperature, the reaction product was dissolved in methanol and analyzed by GC. As a result, the conversion rate of ammonium salt of 1,4-cyclohexane dicarboxylic acid and the yield of 1,4-dicyanocyclohexane were 99.9% and 90.8%, respectively.

As can be appreciated that satisfying results were similarly achieved in Example 3 in which, instead of cyclohexane dicarboxylic acid used in Example 2, ammonium salt thereof was used, 1,4-dicyanocyclohexane can similarly be obtained at a high yield if a salt, for example, ammonium salt, of cyanocyclohexane-1-carboxylic acid is used instead of cyanocyclohexane-1-carboxylic acid used in Example 1 of the cyanation reaction.

Example 4

In Example 4, dicyanocyclohexane was obtained by cyanating cyanocyclohexane-1-carboxylic acid without using a solvent.

(Production of Dicyanocyclohexane by Using Cyanocyclohexane-1-Carboxylic Acid in the Absence of Solvent)

88.8 g of 4-cyanocyclohexane-1-carboxylic acid and 0.2 g of zinc oxide were fed into a 300-mL five-necked separable flask equipped with a stirring blade, a gas feeding pipe capable of changing the feeding height, a thermocouple and a dehydrator. Subsequently, the temperature was raised while introducing nitrogen gas (feeding rate 34 ml/min) into the flask via the gas feeding pipe placed above the liquid surface. Once the temperature of the reaction system reached 300° C. while stirring at 300 rpm, the gas inlet was brought down into the reaction solution to initiate ammonia gas bubbling (feeding rate 174 ml/min), which was considered as the start time of the cyanation reaction. Stirring was carried out for 7 hours while maintaining the reaction temperature at 300° C.

At the end of the reaction, the reaction system was left to cool to room temperature, the reaction product was dissolved in methanol and analyzed by GC. As a result, the conversion rate of 4-cyanocyclohexane-1-carboxylic acid and the yield of 1,4-dicyanocyclohexane were 99.9% and 90.2%, respectively.

Comparative Example 1

In Comparative example 1, 1,4-cyclohexane dicarboxylic acid was cyanated in the absence of a solvent.

(Production of Dicyanocyclohexane by Using 1,4-Cyclohexane Dicarboxylic Acid in the Absence of Solvent)

50.1 g of 1,4-cyclohexane dicarboxylic acid and 0.2 g of zinc oxide were fed into a 300-mL five-necked separable flask equipped with a stirring blade, a gas feeding pipe capable of changing the feeding height, a thermocouple and a dehydrator. Subsequently, the temperature was raised while introducing nitrogen gas (feeding rate 34 ml/min) into the flask via the gas feeding pipe placed above the liquid surface. Once the temperature of the reaction system reached 300° C. while stirring at 300 rpm, the gas inlet was brought down into the reaction solution to initiate ammonia gas bubbling (feeding rate 174 ml/min), which was considered as the start time of the cyanation reaction. Since ammonia gas feeding generated water as a by-product, stirring became difficult due to a solid precipitate after stirring at 300° C. for 2 hours although reaction was confirmed. Thus, the reaction was stopped. This stirring defect was presumably caused because heating caused transformation of 1,4-cyclohexane dicarboxylic acid was into a trans isomer that had a melting point exceeding 300° C.

The above-described results, especially, comparison between the results from Example 4 and Comparative example 1 showed that cyanation can proceed smoothly without using a solvent and dicyanocyclohexane can be produced efficiently by using cyanocyclohexane-1-carboxylic acid whose melting point is lower than the reaction temperature as a raw material.

INDUSTRIAL APPLICABILITY

The present invention can provide a novel method for producing dicyanocyclohexane according to which the efficiency and the yield can be enhanced since generation of a by-product that is hard to separate can be suppressed and steps of dissolving a raw material substance and the like are not required. Furthermore, since dicyanocyclohexane can be a raw material of bis(aminomethyl)cyclohexane that is useful as a precursor of a polyamide, a polyurethane or the like used as an optical material such as a plastic lens, a prism, an optical fiber, an information recording substrate or a filter, it is industrially applicable in such industrial fields.

The invention claimed is:

1. A method for producing dicyanocyclohexane, comprising:
   isolating a cyanocyclohexane-1-carboxylic acid and/or a salt thereof as a raw material; and
   contacting the cyanocyclohexane-1-carboxylic acid and/or a salt thereof with an ammonia source to obtain dicyanocyclohexane by a cyanation reaction.

2. The method of claim 1, wherein the cyanocyclohexane-1-carboxylic acid is present, and the cyanocyclohexane-1-carboxylic acid comprises at least one selected from the group consisting of 2-cyanocyclohexane-1-carboxylic acid, 3-cyanocyclohexane-1-carboxylic acid, and 4-cyanocyclohexane-1-carboxylic acid.

3. A method for producing dicyanocyclohexane, comprising:
   heating a cyclohexane dicarboxylic acid and/or a salt thereof and dicyanocyclohexane to obtain a mixture comprising the cyanocyclohexane-1-carboxylic acid and/or a salt thereof, the cyclohexane dicarboxylic acid and/or a salt thereof, and the dicyanocyclohexane such that a weight ratio of dicyanocyclohexane and cyclohexane dicarboxylic acid and/or a salt thereof is in a range of 0.5 to 3.9; and
   contacting the cyanocyclohexane-1-carboxylic acid and/or a salt thereof with an ammonia source to obtain dicyanocyclohexane by a cyanation reaction.

4. The method of claim 3, wherein prior to the heating, the mixture comprises the dicyanocyclohexane and the cyclohexane dicarboxylic acid and/or a salt thereof at the weight ratio of in a range of 0.7 to 2.4.

5. The method of claim 3, wherein, in the heating, the amount of the cyanocyclohexane-1-carboxylic acid and/or salt thereof produced by the heating is in a range of 20 to 100 mol % relative to the amount of the cyclohexane dicarboxylic acid before the heating.

6. The method of claim 1, wherein a catalyst comprising at least one selected from the group consisting of zinc oxide, tin oxide, and iron oxide is used in the cyanation reaction.

7. The method of claim 1, wherein the ammonia source comprises at least one selected from the group consisting of ammonia, urea, ammonium hydrogen carbonate, and ammonium carbonate.

8. The method of claim 1, wherein prior to the contacting, a mole ratio between the ammonia source and the cyanocyclohexane-1-carboxylic acid and/or a salt thereof is in a range of 0.1 to 5.

9. The method of claim 1, wherein a boiling point of at least one solvent in the cyanation reaction is 600° C. or lower.

10. The method of claim 1, wherein prior to the contacting, a weight ratio of a solvent in the cyanation reaction to the cyanocyclohexane-1-carboxylic acid and/or a salt thereof is 10 or less.

11. The method of claim 1, wherein a reaction temperature in the cyanation reaction is in a range of 150° C. to 350° C.

12. The method of claim 1, wherein a reaction pressure in the cyanation reaction is in a range of 0.001 MPa to 10 MPa.

13. The method of claim 1, wherein a salt of the cyanocyclohexane-1-carboxylic acid is contacted, and the salt of the cyanocyclohexane-1-carboxylic acid comprises an ammonium salt.

14. The method of claim 3, wherein a salt of the cyclohexane dicarboxylic acid is heated, and the salt of the cyclohexane dicarboxylic acid comprises an ammonium salt.

15. A method for producing bis(aminomethyl)cyclohexane, comprising:
   subjecting a dicyanocyclohexane to a hydrogenation reaction to obtain bis(aminomethyl)cyclohexane,
   wherein the dicyanocyclohexane is produced by a process comprising the method of claim 1.

16. The method of claim 2, wherein a catalyst comprising at least one selected from the group consisting of zinc oxide, tin oxide, and iron oxide is used in the cyanation reaction.

17. The method of claim 2, wherein the ammonia source comprises at least one selected from the group consisting of ammonia, urea, ammonium hydrogen carbonate, and ammonium carbonate.

18. The method of claim 2, wherein prior to the contacting, a mole ratio between the ammonia source and the cyanocyclohexane-1-carboxylic acid and/or a salt thereof is in a range of 0.1 to 5.

19. The method of claim 2, wherein a boiling point of at least one solvent in the cyanation reaction is 600° C. or lower.

20. The method of claim 2, wherein prior to the contacting, a weight ratio of a solvent in the cyanation reaction to the cyanocyclohexane-1-carboxylic acid and/or a salt thereof is 10 or less.

* * * * *